US006419131B1

(12) United States Patent  (10) Patent No.: US 6,419,131 B1
Rix                       (45) Date of Patent:     Jul. 16, 2002

(54) GLOVE DONNING APPARATUS

(76) Inventor: James E. Rix, 4542 N. Lowell Ave., Chicago, IL (US) 60630

( * ) Notice: Subject to any disclaimer, the term of this patent is extended or adjusted under 35 U.S.C. 154(b) by 0 days.

(21) Appl. No.: 09/893,833

(22) Filed: Jun. 28, 2001

(51) Int. Cl.[7] ............................................. A47G 25/80
(52) U.S. Cl. ...................................................... 223/111
(58) Field of Search ............................... 223/111, 120, 223/112, 113, 1

(56)              References Cited
              U.S. PATENT DOCUMENTS

| 349,529 | A | * | 9/1886 | Shelby | 223/120 |
| 390,571 | A | * | 10/1888 | Currie, Jr. | 223/120 |
| 479,481 | A | * | 7/1892 | Willcox | 223/120 |
| 2,412,900 | A | * | 12/1946 | Mayer | 223/68 |
| 4,159,069 | A | | 6/1979 | Poncy et al. | |
| 4,765,520 | A | * | 8/1988 | Barton | 223/111 |
| 4,898,309 | A | | 2/1990 | Fischer | |
| D316,176 | S | | 4/1991 | Fischer | |
| 5,769,289 | A | * | 6/1998 | Lusk | 223/112 |
| 6,053,380 | A | | 4/2000 | Sherrod | |
| 6,193,117 | B1 | | 2/2001 | Poschelk | |
| D440,740 | S | | 4/2001 | Anctil | |
| 6,279,792 | B1 | * | 8/2001 | Neal | 223/111 |

* cited by examiner

Primary Examiner—Bibhu Mohanty
(74) Attorney, Agent, or Firm—Lloyd L. Zickert

(57)           ABSTRACT

A glove donning apparatus for donning a glove with a single hand, which comprises a pair of upstanding elongated bars supported by rods from a stationary member, wherein the bars are shaped and sized so that the glove may be trained over the bars at the open or cuff end of the glove to thereafter hold the glove in position for insertion of the hand.

17 Claims, 6 Drawing Sheets

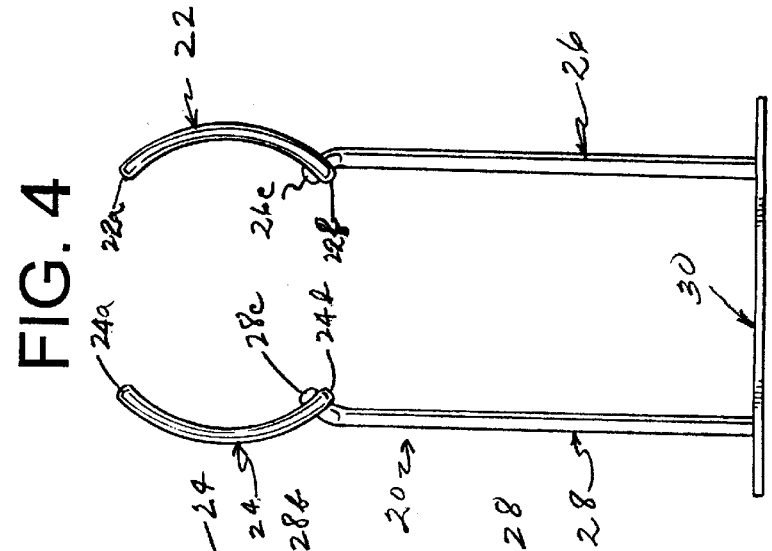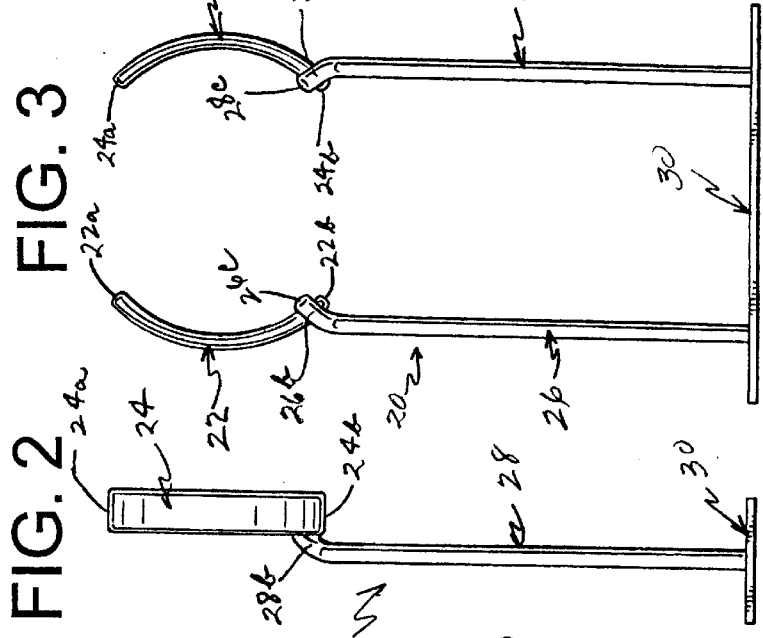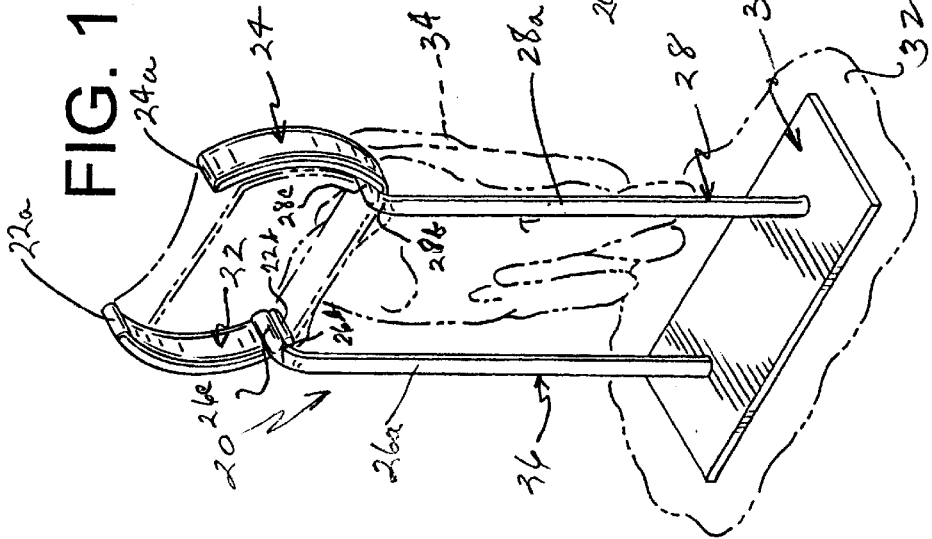

FIG. 8
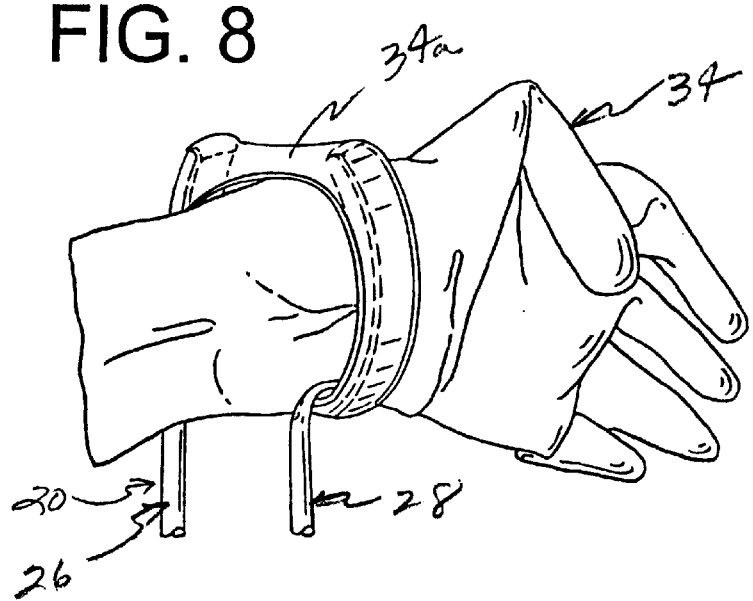
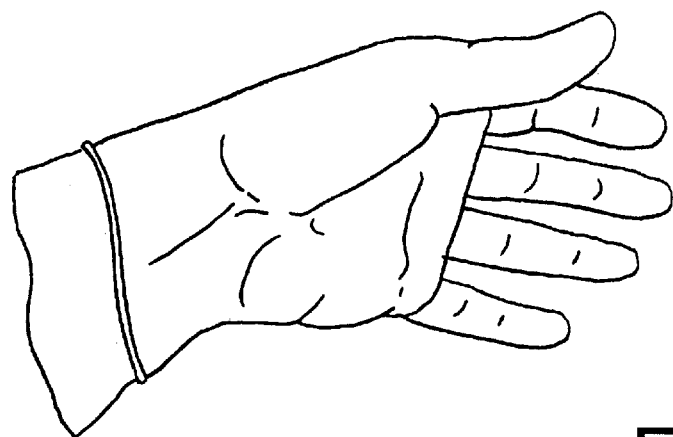
FIG. 9
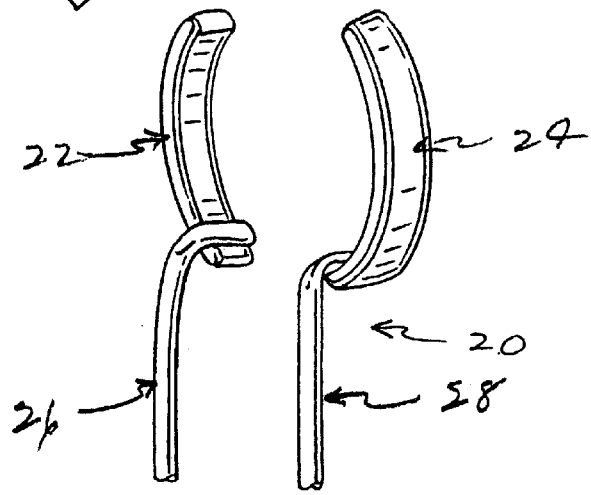

GLOVE DONNING APPARATUS

This invention relates in general to a glove donning apparatus for use by a person in the donning of a glove with a single hand, and more particularly to a glove donning apparatus for donning gloves made of elastic material; and still more particularly to a device for donning elastic medical gloves with a single hand.

BACKGROUND OF THE INVENTION

Heretofore, it has been known to manually don elastic medical examination gloves with the assistance of another person, and sometimes by the person desiring to wear the gloves. Medical examination gloves of the latex or rubber type, both powdered and powderless, are used extensively in doctors' offices and hospitals for the examination of patients, as well as in operatories during surgery. Powder-free gloves are more difficult to don than powdered gloves, and since patients may adversely react to powder, powder-free gloves are generally preferred. Also, dentists and dental hygienists and other dental assistants use rubberized examination gloves in the handling of patients.

It has also been known that great difficulty has also been experienced when a person is donning a double set of gloves, that is, one glove over another glove, in order to guard against needle punctures.

It has also been known to provide glove donning apparatus such as disclosed in U.S. Pat. No. 4,898,309 and U.S. Design Pat. No. 316,176, but these devices are complex in structure, difficult to use, and prone to compromise glove sterility. Donning skin-tight latex or rubber gloves is not only time-consuming but tedious, particularly when it must be done without the assistance of another person.

Moreover, a single-handed person relies on another person to assist in donning medical examination gloves, and it is difficult to accomplish the glove donning operation with heretofore known makeshift devices.

SUMMARY OF THE INVENTION

The glove donning apparatus of the present invention solves the problems heretofore encountered in providing an apparatus that allows a person to don a glove by using a single hand. The present invention is particularly useful in donning both powdered and powderless elastic medical examination gloves that are "skin tight". The glove donning apparatus of the present invention significantly reduces the difficulty of donning a glove by the single hand of a person by providing a flexible two-sided restraining device. This restraining device holds the glove open at the cuff end in a manner that maintains the hygienic integrity of the glove in that the exterior of the glove will not be contaminated. The two-sided restraining device includes a pair of elongated bar members over which the cuff end or mouth end of a rubber glove may be stretched and held in place. The bar members are supported on somewhat flexible rods that extend to a base on a stationary table or bench. Thus, the spaced-apart bar-shaped member may resiliently move toward each other but normally be in a spaced-apart relation.

The glove is primarily engaged at the cuff end at four different spaced-apart points to hold the cuff end or mouth end of the glove open for the insertion of a hand. The restraining bar members hold the glove in position the entire time a person is inserting the hand and fingers into the glove. Once the hand is fully inserted into the glove and the glove is on the hand, manipulation of the arm and hand of the individual can then serve to disengage the cuff end of the glove from the bar-shaped members and free of the donning apparatus.

The bar-shaped members may take any suitable form in that they may be curvate or arcuate in form, or they may be straight. Moreover, they may be formed by the bending of an elongated wire into a loop that enables the loop part of the wire to function as the glove-engaging member.

Most importantly, the glove donning device of the present invention can be used by a person with a single hand, whether that person has two hands or not.

It is therefore an object of the present invention to provide a new and improved glove donning apparatus or device for the donning of elastic rubber gloves that may be donned by a person without the help of another person, and more particularly with the use of only a single hand.

Another object of the present invention is to provide a glove donning device that allows an individual to easily mount the glove on a donning apparatus and thereafter to insert the hand into the glove while using only one hand of the person.

A further object of the present invention is to provide a glove donning apparatus that is very simple in operation and function and which is inexpensive to manufacture while being capable of withstanding the rigors of donning gloves by persons needing to wear examination gloves when in contact with patients.

It is also an object of the present invention to provide a glove donning apparatus that will allow the medical examination gloves to be held and maintained in a sterile condition during the time that the glove is being donned by a person.

Other objects, features and advantages of the invention will be apparent from the following detailed disclosure, taken in conjunction with the accompanying sheets of drawings, wherein like reference numerals refer to like parts.

DESCRIPTION OF THE DRAWINGS

FIG. 1 is a perspective view of the preferred embodiment of the present invention showing a glove donning apparatus with a glove in mounted position in phantom;

FIG. 2 is a side elevational view of the apparatus of FIG. 1;

FIG. 3 is a rear elevational view of the apparatus of FIG. 1;

FIG. 4 is a front elevational view of the apparatus of FIG. 1;

FIG. 5 is a top plan view of the apparatus of FIG. 1;

FIGS. 6 to 9 illustrate the use of the apparatus of the present invention and the embodiment of FIGS. 1 to 5 wherein FIG. 6 shows a person's hand engaging a glove and training a part of the cuff of the glove over one of the bar-shaped members of the apparatus, FIG. 7 shows the person training a further portion of the glove over the second bar member of the apparatus, FIG. 8 shows the glove mounted on the bar-shaped members of the apparatus and the beginning of the insertion of the hand of the person into the glove that is mounted on the apparatus, and FIG. 9 shows the gloved hand when freed from the device;

DESCRIPTION OF THE INVENTION

Figure 6:
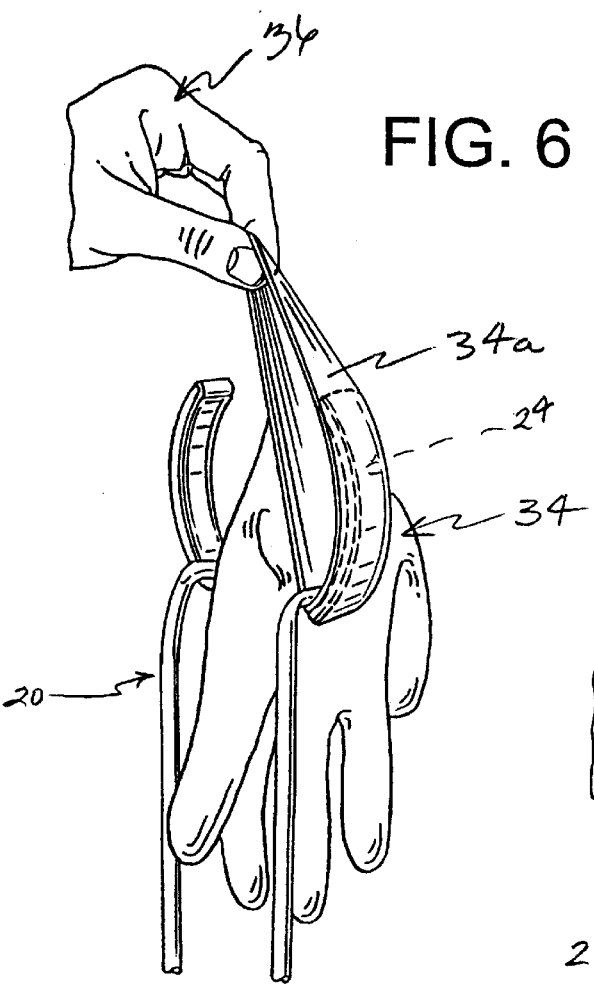

Referring now to the drawings, and particularly to the preferred embodiment of the invention as shown in FIGS. 1 to 5, the glove donning apparatus or device of the present invention is generally indicated by the numeral 20 and includes a pair of spaced-apart glove restraining members or horns 22 and 24 mounted at the upper ends of supporting means in the form of a pair of flexible rods 26 and 28 extending upwardly and attached to a base 30 supported on a suitable table or bench 32. Inasmuch as considerable pressure will be applied to the apparatus during the mounting of a glove in place on the device and also the insertion of a hand into the glove, the base 30 is suitably secured to or clamped to the table or bench 32 against movement and therefore becomes stationary.

Figure 7:
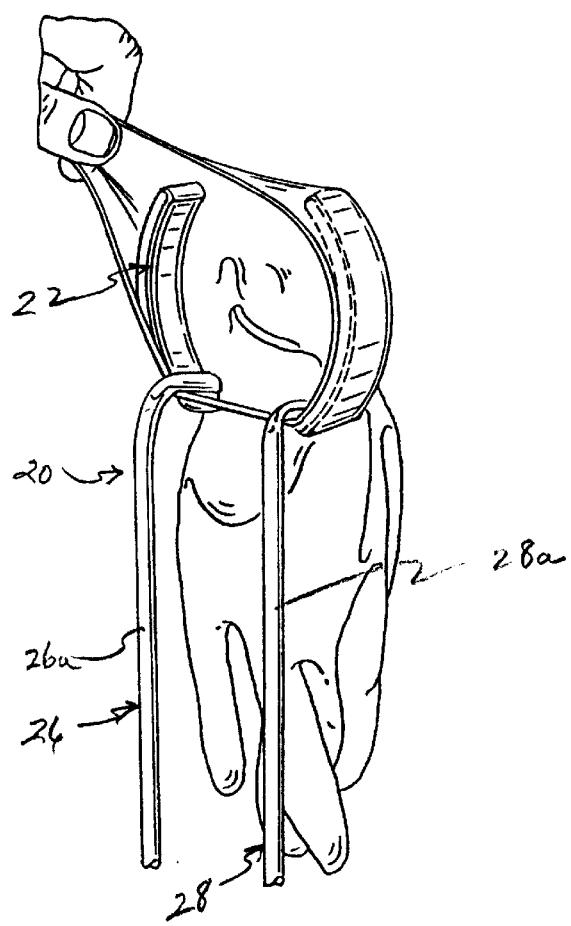

Glove restraining members 22 and 24 are in the form of elongated bar-shaped members that are arcuate in form and symmetrical to each other and of the same length and shape. The symmetry of the glove restraining members presents a mental picture to the person using the device that makes it easier for the mounting of a glove on the members, as shown in FIGS. 6 and 7.

The restraining member or horn 22 includes upper and lower ends 22a and 22b, while the restraining member 24 includes upper and lower ends 24a and 24b. While the upper and lower ends are basically squared off, the corners are rounded such that they present smooth surfaces for engagement by a glove. Similarly, the opposite edges of the bars are also provided with rounded edges in order to be smooth and not tend to catch and/or tear a rubber glove when it is mounted thereon. Likewise, the outer surfaces of the members are smooth. While the members may be made of any suitable material as long as the edges, ends and outer surfaces are smooth, they are preferably made of stainless steel as a welded assembly which would be autoclavable. The restraining members may also be made of plastic material such as polyethylene of the type that is well known, such as used to make polyethylene pipe. As such, these members present a rigid frame that is stiff enough so that they will not collapse upon receiving an elastic glove. In this regard, the smooth surfaces are particularly friendly to rubber or latex medical examination gloves wherein the cuff of the glove may be stretched over the members, as shown in FIGS. 6 and 7, and the smooth surfaces of the members also are friendly to the mounting of powder-free or powderless latex medical examination gloves in readiness for donning by a person.

The rods 26 and 28 of the supporting means for the glove restraining members 22 and 24 are preferably in the form of cylindrical-in-cross-section rods, although they may take any other cross-sectional shape, and each includes a vertically extending portion 26a, 28a, the lower ends of which are suitably secured to the base plate 30. The lower ends may be welded or otherwise secured to the base plate. Thus, the portions 26a and 28a extend upwardly and in aligned relationship to each other and include at their upper ends a slightly inwardly bent portion 26b and 28b connected to laterally extending or horizontally extending attachment portions or stubs 26c and 28c.

Preferably, the supporting rods 26 and 28 are made of stainless steel having the desired flexibility and to which stainless steel restraining members are welded, but it can be appreciated they could be made of any other suitable metal or plastic, if desired. The glove restraining bars 22 and 24 are suitably connected to the horizontal stubs or sections 26c and 28c of the rods 26 and 28 by any suitable means such as by an adhesive that provides a bond that will withstand the forces applied to the glove restraining bars during the mounting of a glove on the bars, the insertion of a hand into the glove, and thereafter the removal of the glove and hand from the area of the bars.

The symmetry of the spaced-apart glove restraining bars 22 and 24 and their supporting rods 26 and 28 can be seen clearly in FIGS. 3 and 4. The mounting of the glove restraining bars onto the rods is such that the lower ends 22b and 24b of the bars 22 and 24 extend slightly below the attaching point to the rod stubs 26c and 28c, so that a part of the glove cuff can be trained thereover. Inasmuch as the restraining members 22 and 24 are barshaped, each end of the members presents two corners over which the cuff end of a glove may be trained when mounting the glove in position on the bars. Further, the innermost corner of the lower ends of the bars, as seen in FIG. 2, is slightly spaced from the vertical sections of the bars, again to facilitate the mounting of the cuff on the restraining bars. It will be appreciated that the restraining bars 22 and 24 are spaced apart such that when a glove is mounted on the bars, the mouth end or cuff end of the glove will be held in open position for the ease of insertion of a hand in the glove during the time the restraining device is holding the glove for donning purposes.

In operation, and with reference to FIGS. 6 to 8, it can be seen that a person may use a single hand for mounting a glove 34 to the glove restraining bars of the apparatus. The hand of a person is shown in FIG. 6 and designated by the numeral 36 and manipulated so that the index finger and the thumb engages a portion of the cuff 34a of the glove 34 to first train one side of the cuff over one of the glove restraining bars. As shown in FIG. 6, the cuff of the glove is mounted over the bar 24 so that it catches or hooks on the lower end of the bar member, after which it can then be stretched to cause the cuff end of the glove to be trained over the opposing restraining bar 22, as shown in FIG. 7. Thereafter, the remaining section of the cuff end is allowed to be relaxed and trained over the upper end of the bar 22, after which the person may begin inserting a hand into the glove, as illustrated in FIG. 8. During the time that a person is inserting a hand into the glove, the cuff end 34a of the glove 34 remains in mounted position wherein the ends of the restraining bars receive a part of the glove and hold it in place as it is stretched between the two bar members. Prior to inserting a hand into the glove, the glove hangs downwardly from the bar members 22 and 24, as shown in FIG. 1 and also as shown in FIG. 7. Because the bar members are offset from the vertical portions 26a and 28a of the rods 26 and 28, the glove will not touch the rods 26 and 28, thereby avoiding contamination of the gloves in the event that there are any contaminants on the rods. Additionally, the lower ends of the gloves will be spaced above the base due to the height of the restraining bars to prevent touching of the finger portions of the glove with the base. Thus, the sterility of the glove is maintained.

Once the hand is fully inserted into the glove by manipulating the arm and hand, the cuff portion of the glove can be easily released from the restraining bars 22 and 24. More specifically, by moving the hand and arm toward one of the bars and downwardly, the lower end of the glove cuff can be released from the lower end of the restraining bar, and then thereafter by tilting the arm upwardly, the upper end of the cuff can be released from the upper end of the restraining bar. Thereafter, the same procedure can be repeated at the other restraining bar. Obviously, these operations could be done in reverse order. It is also possible there might be a need to otherwise manipulate the arm from side to side in order to release the cuff from the restraining bars.

Accordingly, it can be appreciated that a person can use a single hand first to mount the cuff end of a rubber glove over the restraining bars and thereafter insert the hand into the glove and then release the glove from the restraining bars. This operation can be done quickly and efficiently.

It should also be appreciated that the rods 26 and 28 may be mounted such that they may be adjustably positioned relative to each other, thereby accordingly adjustably positioning the restraining bars 22 and 24 from each other where it would be desired to use a different size glove or where it would be needed to accommodate the device for a person with different sized hands. However, the spacing between the restraining bars 22 and 24 is set according to a standard that would meet the needs of those normally using the device for donning gloves.

Additionally, it should be appreciated that a securing system for the lower ends of the rods could be made such that once a glove has been donned by a person, a lever could be tripped to allow the restraining bars 22 and 24 to come toward each other and further facilitate the removal of the glove from the bars.

Figure 10:
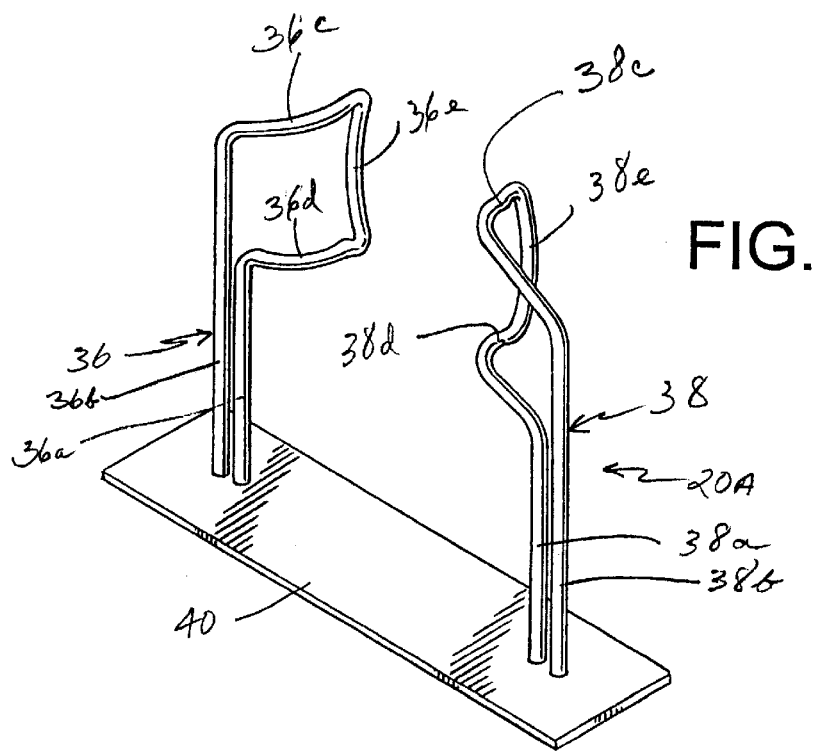
FIG. 10 is a perspective view of a modification of the invention.

Referring now to the embodiment shown in FIG. 10, the glove donning device is generally designated by the numeral 20A and is defined by a pair of upstanding wire members in the form of loops to also form bar-shaped members on which the gloves may be mounted before insertion of a hand into the glove. This device includes upstanding wire loops 36 and 38 supported by and appropriately secured to the base 40.

The upstanding wire loops include, respectively, inner and outer vertically extending parallel portions 36a and 36b and 38a and 38b, upper and lower laterally extending arm portions 36c and 36d and 38c and 38d connected at the upper ends of the vertically extending portions and restraining bar portions 36e and 38e connected at their opposite ends to the laterally extending portions. Since a wire loop stands alone, the various portions are integral with each other.

The wire loops will have some resiliency so that the restraining bar portions 36e and 38e can be moved toward each other during the dismounting of a glove from the device. Preferably, the wire loops are made of stainless steel, although other suitable metals may be used. It will be appreciated that the cuff of a glove would be trained over the restraining bar portions 36e and 38e in a similar manner to the way a glove would be mounted on the glove donning apparatus of FIGS. 1 to 9. Also, removal would be as above described where the glove may be removed from the device after a person has inserted a hand into the glove. These wire loops are spaced apart sufficiently so that when the glove hangs down from the restraining bar portions 36e and 38e, it will be hanging in an area between and spaced from the wire loops and therefore not become contaminated by touching the wire loops. Further, it will be appreciated that the restraining bar portions 36e and 38e would be spaced sufficiently above the base so that the lower end or the tip ends of a glove hanging down would not engage the base 40 or the surface on which the base is mounted.

Figure 11:
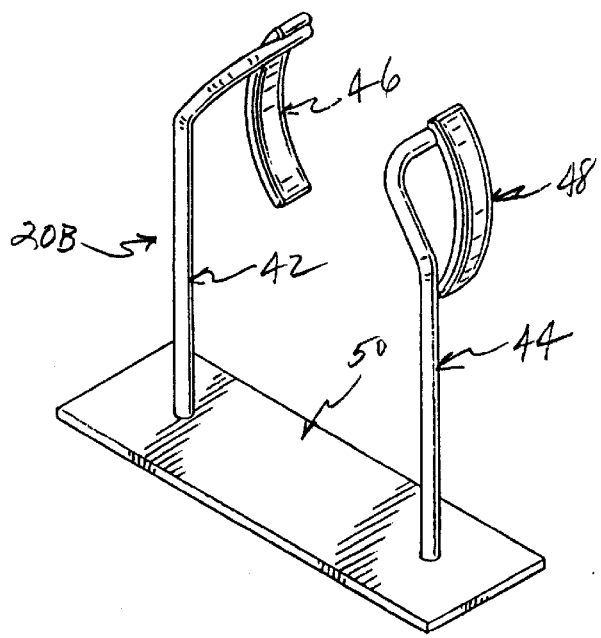
FIG. 11 is a perspective view of a further modification of the invention.

A further embodiment of the invention is shown in FIG. 11 and generally designated by the numeral 20B, which includes upstanding rod supporting members 42 and 44 having bar-shaped glove restraining members or restraining bars 46 and 48 mounted at the upper ends of the rods 42 and 44. As in the other embodiments, the rods 42 and 44 are stationarily mounted on a base member 50. This embodiment differs from the embodiment of FIGS. 1 to 9 in that the supporting rods 42 and 44 are spaced further apart and the glove restraining bars 46 and 48 are secured to studs on the rods adjacent to the upper ends of the bar-shaped glove restraining members. The operation of this device will be the same as that of the device shown in FIGS. 1 to 9.

Figure 12:
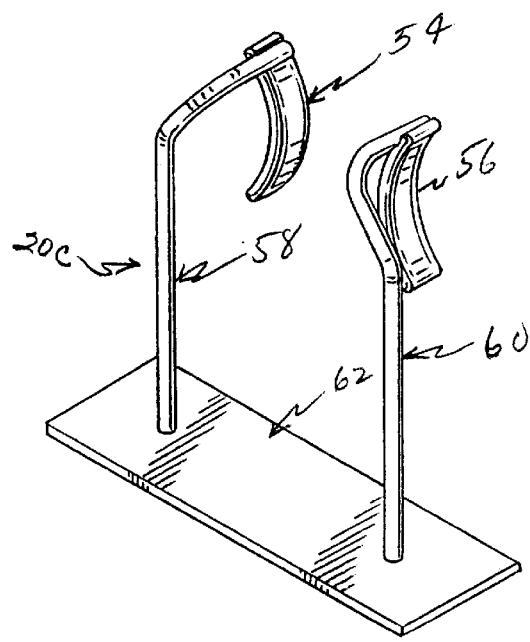
FIG. 12 is a perspective view of a still further modification of the invention.

A further embodiment of the invention is shown in FIG. 12 and generally designed by the numeral 20C, and which differs from the embodiment of FIG. 11 in that the bar-shaped glove restraining members designated 54 and 56, while arcuate in form, are reversed in position such that the convex faces of the members oppose one another. Again, the members 54 and 56 are mounted on stubs at the upper ends of rods 58 and 60 upstanding from base 62. The operation of this embodiment will be the same as the previous embodiments as the upper and lower ends of the bar-shaped members provide ends over which a glove can be trained during mounting a glove on the device and which would serve to hold the cuff of the glove open for a person to extend a hand into the glove.

Figure 13:
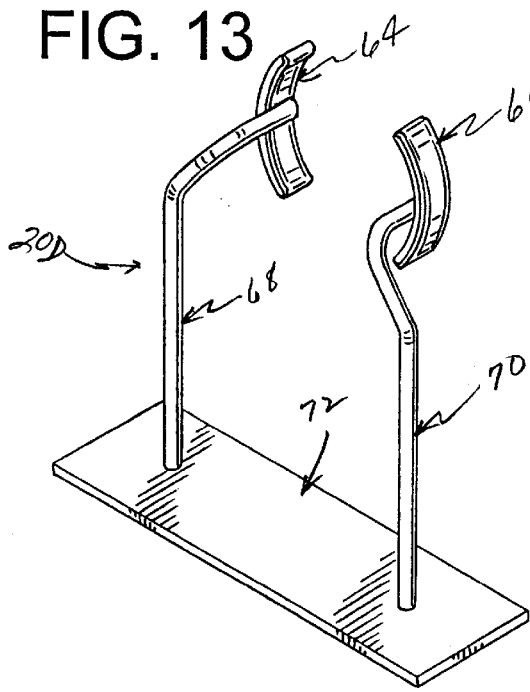
FIG. 13 is a perspective view of a still further modification of the invention.

A further embodiment of the invention is shown in FIG. 13 and generally designed by the numeral 20D, and which includes bar-shaped glove restraining members 64 and 66 of the same type as in the embodiment of FIGS. 1 to 9, 11 and 12. The restraining members 64 and 66 are mounted on stubs at the upper ends of rods 68 and 70 extending upwardly from a base 72. This embodiment differs from the embodiment of FIG. 11 only in that the position of attachment of the bar-shaped glove restraining member 64 and 66 to the laterally extending stub of the rods 68 and 70 is at the center inside position of the members rather than at the upper ends. It will be appreciated that the operation of this embodiment will be substantially the same as that of the embodiment of FIGS. 1 to 9.

Figure 14:
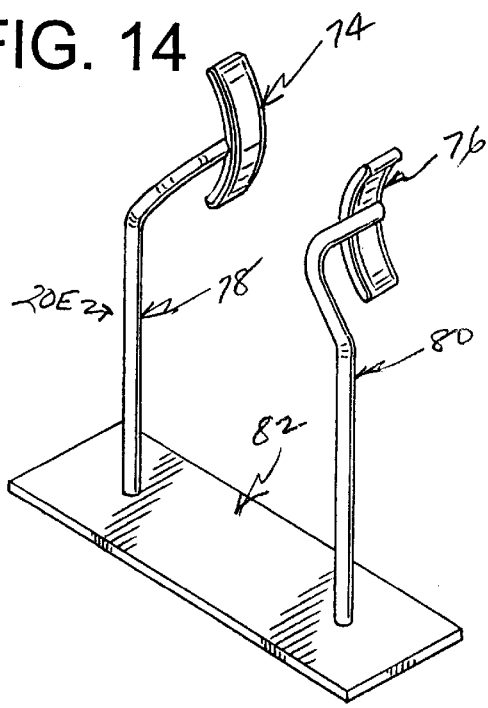
FIG. 14 is a perspective view of a still further modification of the invention.

The embodiment of FIG. 14, generally designated by the numeral 20E, differs from the embodiment of FIG. 13 only in that the bar-shaped glove restraining members 74 and 76 are reversed in position in that the convex sides face each other in a manner similar to the embodiment of FIG. 12. The members or bars 74 and 76 are mounted on lateral extending stubs at the upper ends of rods 78 and 80 carried on the base 82. The operation of this embodiment would be the same as the operation of the embodiment of FIGS. 1 to 9 and also as set forth in connection with the representation of the operation of the embodiment of FIG. 12.

Figure 15:
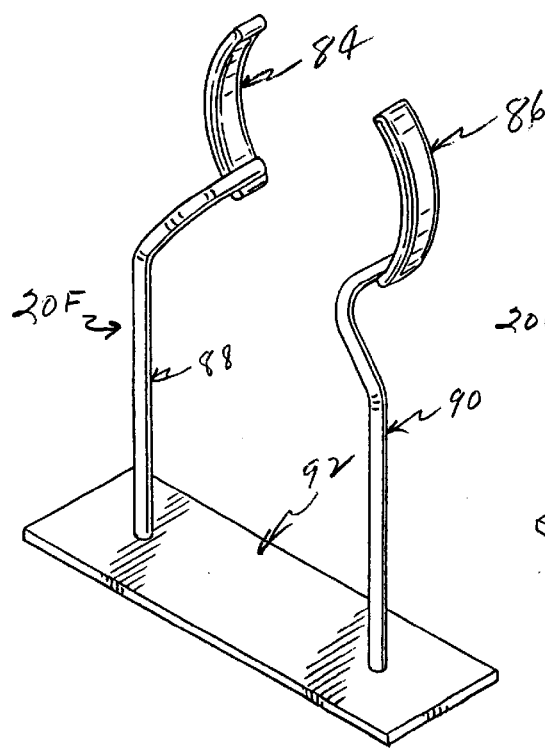
FIG. 15 is a perspective view of a still further modification of the invention.

A further embodiment of the invention is shown in FIG. 15 and generally indicated by the numeral 20F, which differs from the embodiment of FIG. 13 only in that the bar-shaped glove restraining members 84 and 86 are mounted to the stub ends of rods 88 and 90 at the lower ends of the bar-shaped members. Rods 88 and 90 extend upwardly from and are secured to the base 92. It will be appreciated that the operation of this embodiment will be the same as the other embodiments in that the cuff of a glove will be trained over the restraining members 84 and 86, after which a person can insert a hand into the glove and then thereafter remove the glove and hand from the restraining members.

Figure 16:
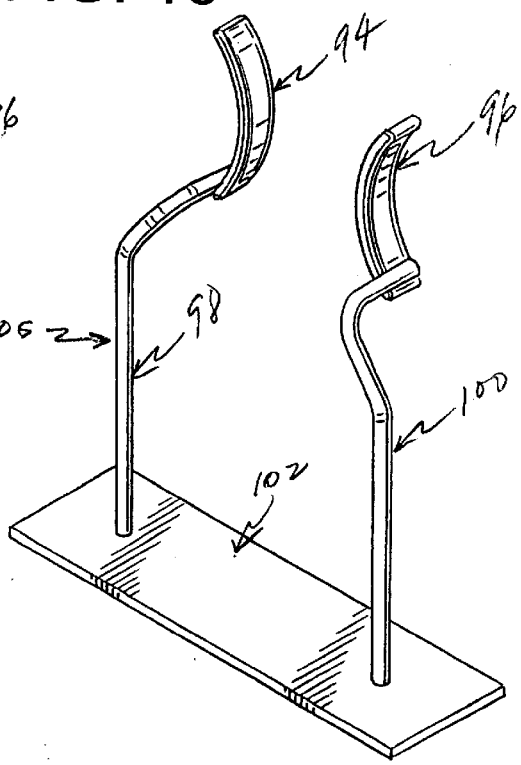
FIG. 16 is a perspective view of a still further modification of the invention.

A further embodiment of the invention is shown in FIG. 16 and generally indicated by the number 20G, and differs from the embodiment of FIG. 15 only in that the bar-shaped glove restraining members 94 and 96 mounted on the stub ends of rods 98 and 100, respectively, are reversed in position from the position of the members 84 and 86 in FIG. 15 and where the convex sides face each other. The rods extend upwardly from the base 102. Further, this embodiment differs from the embodiment of FIG. 14 only in that the bar-shaped glove restraining members 94 and 96 are mounted to the stub ends of the rods at their lower ends rather than in the intermediate area. With respect to any of the embodiments, it can be appreciated that the stub ends can be mounted on the inside or the outside of any of the bar-shaped glove restraining members. The operation of this embodiment will be the same as the other embodiments when a person is donning a glove and then thereafter removing the glove and hand from the device.

Figure 17:
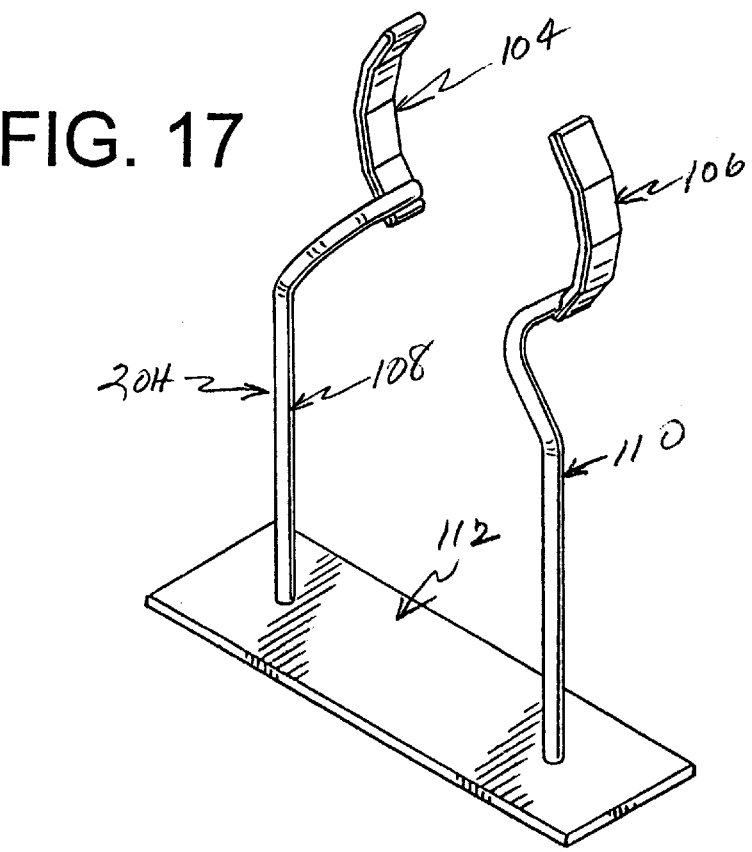
FIG. 17 is a perspective view of a still further modification of the invention.

The embodiment generally designated by the numeral 20H in FIG. 17 differs from the embodiment of FIG. 15 only in that the bar-shaped glove restraining members 104 and 106 are polygonally shaped rather than being arcuately shaped. It will be appreciated that the shape of the bar-shaped members, while being preferred to be arcuately shaped and positioned as shown in the embodiment of FIGS. 1 to 9, could be shaped otherwise. The bar-shaped glove restraining members 104 and 106 are mounted on laterally extending stubs of rods 108 and 110 that extend upwardly and are mounted on the base 112. Except for the configuration of the bar-shaped glove restraining members 104 and 106, this embodiment is the same as the embodiment of FIG. 15. It will be appreciated that the actual shape of the bar-shaped restraining members may take any number of shapes and still provide the four-corner arrangement over which the glove may be trained when mounting it on the glove donning device. Otherwise, it will be appreciated that the operation of the embodiment 20H will be the same as the operation of the other embodiments and particularly the embodiment of FIGS. 1 to 9.

Figure 18:
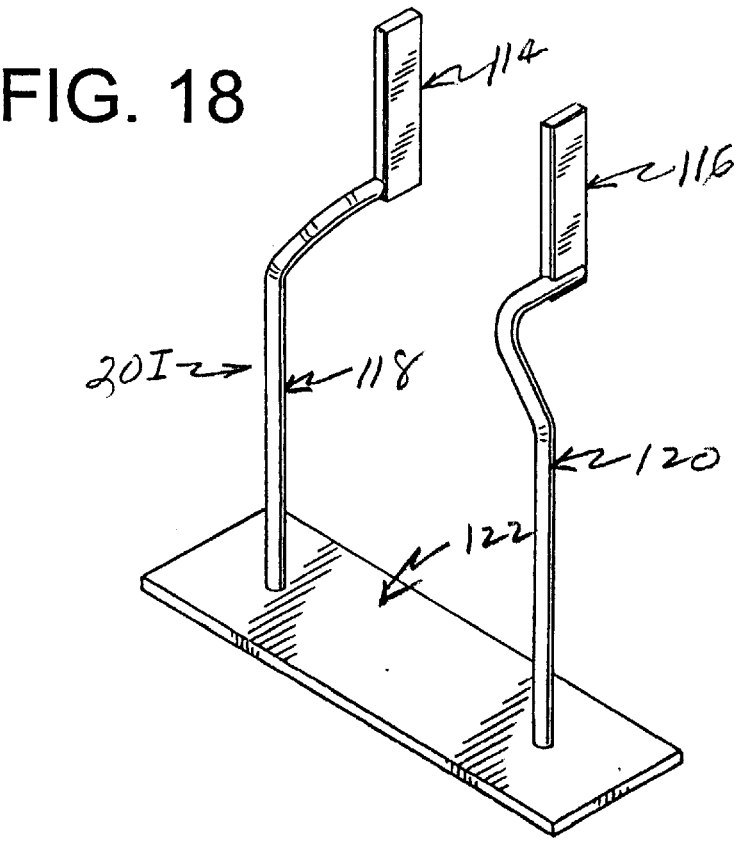
FIG. 18 is a perspective view of a still further modification of the invention.

A still further embodiment of the invention is shown in FIG. 18, wherein the glove donning apparatus is generally designated 201 and includes bar-shaped glove restraining members 114 and 116 mounted at their lower ends to stubs of upstanding rods 118 to 120 stationarily fixed to a base 122. Except for the configuration of the bar-shaped glove restraining members, this embodiment operates the same as the other embodiments. Again, the bar-shaped restraining members 114 and 116 provide the four-corner glove mounting points for holding the glove in open position at the cuff end for purposes of inserting a hand into the glove. Again, the rubber glove will be caught or hooked over the corners of the straight bar-shaped glove restraining members when initially mounting the glove on the device for purposes of allowing a hand to be inserted into the glove. As with respect to the embodiments of FIGS. 10 to 17, the rods 118 and 120 are spaced far enough apart so that when the glove is mounted on the restraining members, it will hang downwardly into an open area laterally from the rods and also in spaced relation from the rods and the base so that the glove will not become contaminated with the rods or the base. Otherwise, the operation of this embodiment is the same as the operation of the other embodiments.

From the foregoing, it can be appreciated that all the embodiments have in common the inclusion of bar-shaped glove restraining members or restraining bars having a four-point contact with the cuff end of the glove to hold the cuff end open during the time a person inserts a hand into the glove. In the embodiments which include bar-shaped restraining members that are outwardly bowing from each other, such as the embodiment of FIGS. 1 to 9 and the embodiments of FIGS. 10, 11, 13, 15 and 17, in addition to the four-point contact made with the cuff of the glove, the glove cuff also is stretched outwardly along the restraining members to provide additional room for a hand to be inserted into the glove.

It can also be appreciated that the glove donning apparatus of the present invention could be used for other types of gloves such as those worn to keep hands warm or otherwise protected and for persons who are handicapped and have the use of only one hand. In this instance, the surfaces of the bar-shaped glove restraining members would preferably be roughened in order to provide an additional contact engagement with the cuff of the glove to hold it in place during the time a hand is inserted into the glove.

It will be understood that modifications and variations may be effected without departing from the scope of the novel concepts of the present invention, but it is understood that this application is to be limited only by the scope of the appended claims.

What is claimed is:

1. A glove donning apparatus comprising:
   a pair of substantially vertically extending spaced apart elongated bar-shaped members over which the open end of a glove may be mounted to hold the glove open during insertion of a hand into the glove,
   each bar-shaped member including spaced apart ends over which part of the open end of the glove is releasably held in a four corner arrangement,
   means for supporting said members on a stationary base,
   said supporting means including substantially vertically extending rods, and stabs laterally extending from the rods and to which the bar-shaped members are attached such as to offset the bar-shaped members from the rods, wherein the open end of the glove when mounted on the bar-shaped members extends substantially vertically so that a hand may be inserted into the glove along a substantially horizontal path.

2. The glove donning apparatus of claim 1, wherein said bar-shaped members are generally U-shaped.

3. The glove donning apparatus of claim 2, wherein said bar-shaped members are generally crescent-shaped.

4. The glove donning apparatus of claim 2, wherein said bar-shaped members are generally arcuately shaped.

5. The glove donning apparatus of claim 2, wherein said bar-shaped members are generally polygonally shaped.

6. The glove donning apparatus of claim 2, wherein said bar-shaped members are generally substantially straight.

7. The glove donning apparatus of claim 6, wherein said rods are resilient to allow some resilient movement between the bar-shaped members during the mounting of a glove thereon and the removing of a glove therefrom.

8. The glove donning apparatus of claim 7, wherein the bar-shaped members are attached to the stubs adjacent one end of the bar-shaped members.

9. The glove donning apparatus of claim 8, wherein the bar-shaped members are attached to the stubs adjacent the upper end of the bar-shaped members.

10. The glove donning apparatus of claim 8, wherein the bar-shaped members are attached to the stubs adjacent the lower end of the bar-shaped members.

11. The glove donning apparatus of claim 7, wherein the bar-shaped members are attached to the stubs intermediate the ends of the bar-shaped members.

12. The glove donning apparatus of claim 1, wherein the supporting means and the bar-shaped members are formed by a wire loop with upstanding portions extending upwardly from a stationary base.

13. The glove donning apparatus of claim 1, wherein the bar-shaped members have smooth surfaces.

14. The glove donning apparatus of claim 1, wherein the bar-shaped members have roughened surfaces.

15. A device for holding a rubber glove having a cuff end of said glove during insertion of a hand into the glove comprising:

spaced-apart substantially vertically extending restraining members over which the cuff end of the glove may be mounted to support the glove with the cuff end open so that a hand may be inserted into the glove, and means supporting the restraining members including upstanding slightly flexible rods extending upwardly from a stationary base such that when a glove is mounted on the restraining members and hangs downwardly therefrom the glove will not touch the supporting members or the base, and said rods including laterally extending stubs onto which the restraining members are offset mounted from the rods so that the cuff end of the glove will hook over the restraining members and be held in place on the restraining members during insertion of a hand into the glove, whereby the cuff end of the glove extends substantially vertically and hand insertion is along a substantially horizontal path.

16. The device of claim 15, and said restraining members being formed to define a four corner arrangement for receiving the cuff end of the glove.

17. The device of claim 15, wherein the restraining members are formed to be outwardly bowing from each other to provide additional room for a hand to be inserted into a glove.

* * * * *